(12) United States Patent
Nozato et al.

(10) Patent No.: US 11,273,244 B2
(45) Date of Patent: Mar. 15, 2022

(54) DIALYSIS DEVICE

(71) Applicant: SHIBUYA CORPORATION, Kanazawa (JP)

(72) Inventors: Nobuyuki Nozato, Kanazawa (JP); Shingo Saito, Kanazawa (JP)

(73) Assignee: SHIBUYA CORPORATION, Kanazawa (JP)

( * ) Notice: Subject to any disclaimer, the term of this patent is extended or adjusted under 35 U.S.C. 154(b) by 373 days.

(21) Appl. No.: 16/225,680

(22) PCT Filed: Jun. 15, 2017

(86) PCT No.: PCT/JP2017/022066
§ 371 (c)(1),
(2) Date: Dec. 19, 2018

(87) PCT Pub. No.: WO2018/008349
PCT Pub. Date: Jan. 11, 2018

(65) Prior Publication Data
US 2019/0231959 A1    Aug. 1, 2019

(30) Foreign Application Priority Data
Jul. 4, 2016    (JP) ............................. JP2016-132523

(51) Int. Cl.
*A61M 1/16* (2006.01)
*B01F 21/20* (2022.01)
(Continued)

(52) U.S. Cl.
CPC ............ *A61M 1/1666* (2014.02); *A61M 1/16* (2013.01); *B01F 21/22* (2022.01);
(Continued)

(58) Field of Classification Search
CPC ......... A61M 1/1666; A61M 2205/3331; B01F 1/0027; B01F 15/00162; B01F 15/00344; B01F 2215/0034
See application file for complete search history.

(56) References Cited

U.S. PATENT DOCUMENTS 4,784,495 A * 11/1988 Jonsson .............. A61M 1/1674
366/151.1
5,972,223 A * 10/1999 Jonsson ................ A61L 2/0023
137/88
2015/0174310 A1* 6/2015 Mishima ............ B01D 19/0042
210/180

FOREIGN PATENT DOCUMENTS

JP     63-194666 A    8/1988
JP     2009-539522 A    11/2009
(Continued)

OTHER PUBLICATIONS

English International Search Report for corresponding PCT/JP2017/022066, dated Aug. 29, 2017 (2 pgs).
(Continued)

*Primary Examiner* — Patrick Orme
(74) *Attorney, Agent, or Firm* — Flynn Thiel, P.C.

(57) ABSTRACT

This dialysis device is configured so that residual liquid in a powder container 42 and a bypass path 51 can be drained. Accordingly, the dialysis device is provided with: a first liquid draining path 71 connecting a clean water supply path 31 to a stock solution supply path 44 on the upstream side of a liquid feed pump 33; a second liquid draining path 72 connecting the clean water supply path to a dialysate discharge path 32 on the downstream side of the liquid feed pump; and an opening path 77 allowing a branch path 43 to communicate with the outer space by opening an on-off valve 78. By opening the on-off valve of the opening path and actuating the liquid feed pump, a liquid in the powder
(Continued)

container 42 and a liquid in the bypass path 51 can be discharged through the first liquid draining path and the second liquid draining path.

5 Claims, 3 Drawing Sheets

(51) Int. Cl.
    *B01F 35/21*     (2022.01)
    *B01F 35/221*     (2022.01)
    *B01F 101/00*     (2022.01)

(52) U.S. Cl.
    CPC ...... *B01F 35/2113* (2022.01); *B01F 35/2211* (2022.01); *A61M 2205/3331* (2013.01); *B01F 2101/2202* (2022.01)

(56) References Cited

FOREIGN PATENT DOCUMENTS

| | | |
|---|---|---|
| JP | 2012-170722 A | 9/2012 |
| JP | 2016-059684 A | 4/2016 |
| WO | WO 2007/144427 A2 | 12/2007 |
| WO | WO 2011/000347 A1 | 1/2011 |

OTHER PUBLICATIONS

Japanese International Search Report and Written Opinion for corresponding PCT/JP2017/022066, dated Aug. 29, 2017 (9 pgs).

\* cited by examiner

DIALYSIS DEVICE

TECHNICAL FIELD

The present invention relates to a dialysis device, and more particularly relates to a dialysis device including stock solution producing means that produces a stock solution of dialysate by supplying clean water into a powder container.

BACKGROUND ART

Conventionally, as a dialysis device, there is known a dialysis device including stock solution producing means producing a stock solution of dialysate, dialysate producing means producing the dialysate by mixing clean water supplied by a liquid feed pump provided in a clean water supply path and the stock solution supplied from the stock solution producing means via a stock solution supply path, a dialysate supply path supplying the dialysate to a dialyzer from the dialysate producing means, and a dialysate discharge path discharging used dialysate from the dialyzer, the stock solution producing means having a powder container attachably and detachably connected to a branch path branched from the clean water supply path and the stock solution supply path, producing the stock solution by dissolving dialysate producing powder in the powder container by the clean water supplied from the branch path, and supplying the produced stock solution to the dialysate producing means via the stock solution supply path (Patent Document 1).

PRIOR ART DOCUMENTS

Patent Document 1
Japanese Laid-Open Patent Application No. 2012-170722

SUMMARY OF THE INVENTION

The powder container is detached from the branch path and stock solution supply path after dialytic treatment, and at this time, the stock solution remaining in the powder container resultantly leaks to the outside.

Further, before starting dialytic treatment, by causing the branch path and stock solution supply path to communicate with each other via a bypass path, a dialysis circuit including the branch path and the stock solution supply path can be cleaned in this state, but when the bypass path is detached from the branch path and the stock solution supply path after cleaning, a cleaning solution remaining in the bypass path leaks to the outside.

In the light of the circumstances like this, the present invention provides a dialysis device capable of preventing a stock solution from leaking to an outside from the powder container when the powder container is detached from a branch path and a stock solution supply path.

Further, the present invention provides a dialysis device capable of preventing a cleaning solution from leaking to the outside from a bypass path when the bypass path is detached from the branch path and the stock solution supply path.

One aspect of the invention is a dialysis device including stock solution producing means producing a stock solution of dialysate, dialysate producing means producing the dialysate by mixing clean water supplied by a liquid feed pump provided in a clean water supply path and the stock solution supplied from the stock solution producing means via a stock solution supply path, a dialysate supply path supplying the dialysate to a dialyzer from the dialysate producing means, and a dialysate discharge path discharging used dialysate from the dialyzer, the stock solution producing means having a powder container attachably and detachably connected to a branch path branched from the clean water supply path and the stock solution supply path, producing the stock solution by dissolving dialysate producing powder in the powder container by the clean water supplied from the branch path, and supplying the produced stock solution to the dialysate producing means via the stock solution supply path, characterized in that a first liquid draining path connecting the clean water supply path at an upstream side of the liquid feed pump to the stock solution supply path, a second liquid draining path connecting the clean water supply path at a downstream side of the liquid feed pump to the dialysate discharge path, an opening path causing the branch path to communicate with an external space by opening an on-off valve, and control means controlling the liquid feed pump and the on-off valve are provided, and the control means drains a liquid in the powder container via the first liquid draining path and the second liquid draining path by opening the on-off valve in the opening path and operating the liquid feed pump.

Further, another aspect of the invention is characterized in that a bypass path connecting the stock solution supply path and the branch path in a state where the powder container is detached from the stock solution supply path and the branch path is provided, the control means drains a liquid in the bypass path via the first liquid draining path and the second liquid draining path by opening the on-off valve in the opening path and operating the liquid feed pump in a state where the bypass path is connected to the stock solution supply path and the branch path.

Further, before the powder container is detached from the branch path and the stock solution supply path, the liquid in the powder container can be drained via the first liquid draining path and the second liquid draining path by opening the on-off valve of the opening path and operating the liquid feed pump by the control means, so that if the powder container is detached from the branch path and the stock solution supply path thereafter, the stock solution can be prevented from leaking to the outside from the inside of the powder container.

Further, before the bypass path is separated from the branch path and the stock solution supply path, the liquid in the bypass path can be drained via the first liquid draining path and the second liquid draining path by opening the on-off valve of the opening path and operating the liquid feed pump by the control means, so that if the bypass path is separated from the branch path and the stock solution supply path thereafter, the liquid can be prevented from leaking to the outside from the inside of the bypass path.

DETAILED DESCRIPTION

Figure 1:
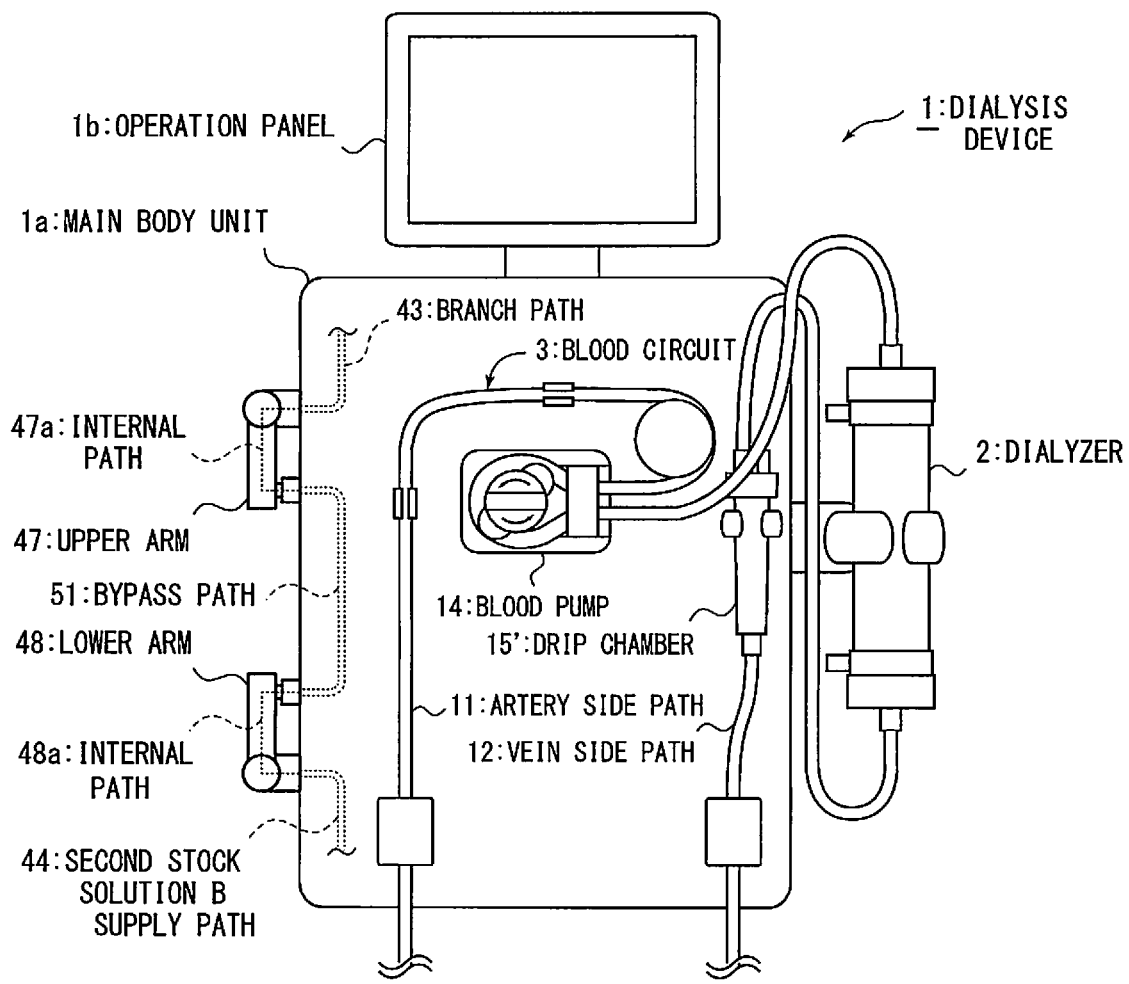
FIG. 1 is an external view illustrating an embodiment of the present invention.

Explaining the present invention with respect to an illustrated embodiment hereinafter, FIG. 1 illustrates an external appearance of a dialysis device 1 that performs dialytic treatment. The dialysis device 1 operates by being supplied with power from a power supply such as a receptacle of a hospital, and has its operation controlled by control means (not illustrated) provided inside.

The dialysis device 1 includes a dialyzer 2 held at an outside of a main body unit 1a, a blood circuit 3 connected to the dialyzer 2, and a dialysate circuit 4 (FIG. 3) provided inside the main body unit 1a. The dialyzer 2 is detachably attached to the main body unit 1a.

The control means and includes a screen display type operation panel 1b, buttons, icons and messages necessary for an operation are displayed on the screen, and an operation of the dialysis device 1 and setting of various parameters can be performed.

Figure 3:
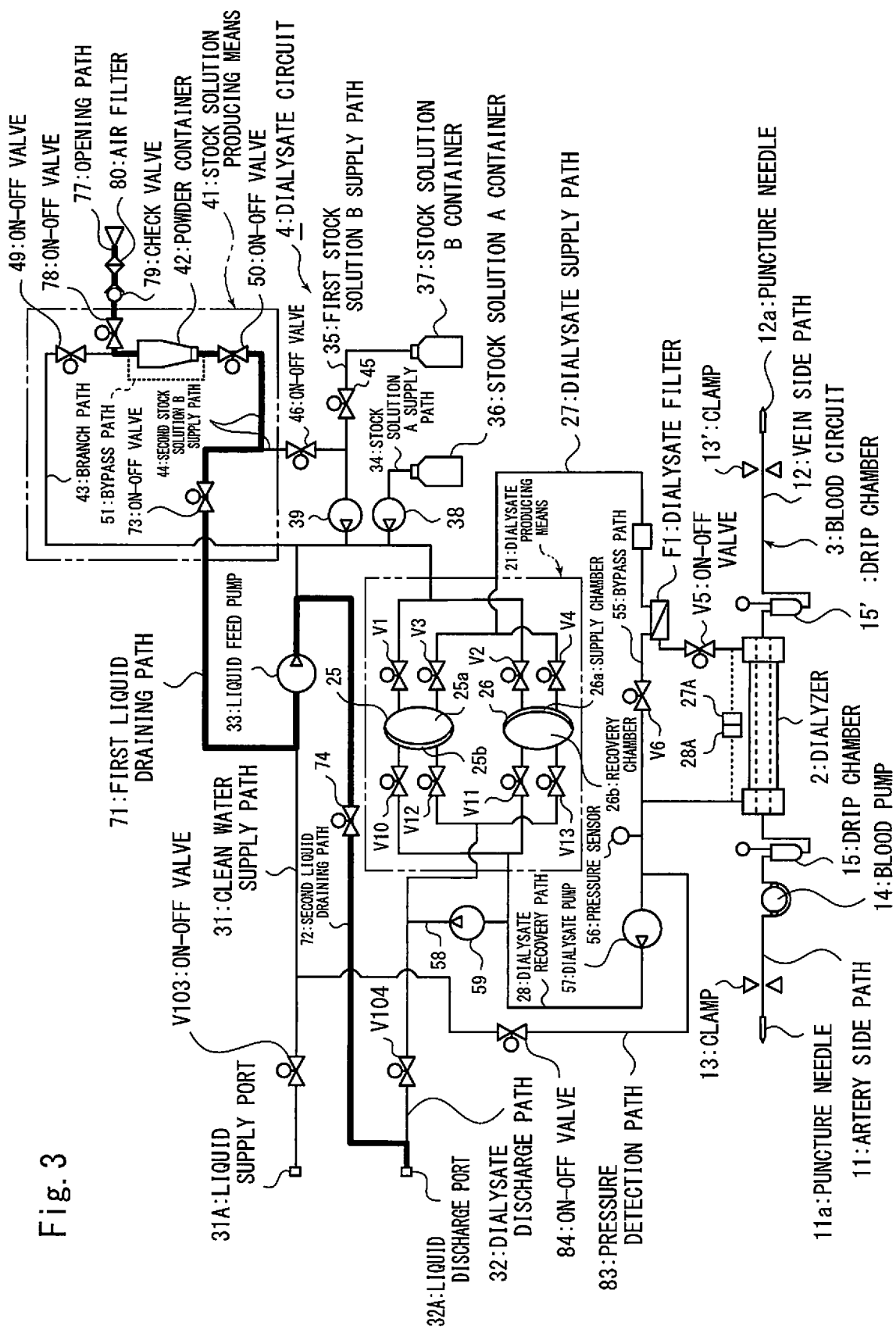
FIG. 3 is a diagram illustrating a dialysate circuit in a dialysis device illustrated in FIG. 1, in which a thick line shows a state of an operation of liquid draining from the powder container 42.

As illustrated in FIG. 1 and FIG. 3, the blood circuit 3 includes an artery side path 11 connected to a blood vessel of a patient to supply blood to the dialyzer 2, and a vein side path 12 that returns blood to the patient from the dialyzer 2, and these paths are formed of a resin tube.

As illustrated in FIG. 3, a puncture needle 11a to be punctured in a blood vessel of a patient is provided at one end of the artery side path 11, and the other end is connected to the dialyzer 2. In order from the puncture needle 11a, a clamp 13 that closes the artery side path 11, a blood pump 14 that feeds blood, and a drip chamber 15 are disposed. The blood pump 14 is a roller pump that feeds a liquid by squeezing a tube, has an operation controlled by the control means, and is capable of feeding blood to the dialyzer 2 from the patient not illustrated.

One end of the vein side path 12 is connected to the dialyzer 2 while a puncture needle 12a to be punctured in a blood vessel of the patient is provided at the other end, and in order from the dialyzer 2, a drip chamber 15', and a clamp 13' that closes the vein side path 12 are disposed.

The dialysate circuit 4 includes a dialysate producing means 21 that produces dialysate from clean water, a stock solution A and a stock solution B, and the dialysate producing means 21 includes a first dialysate chamber 25 and a second dialysate chamber 26 of the same shape. The respective dialysate chambers 25 and 26 have insides divided into two chambers by diaphragms, one of these chambers is a supply chamber 25a and 26a for producing a fresh dialysate to supply the dialysate, and the other of these chambers is a recovery chamber 25b and 26b for recovering used dialysate.

The fresh dialysate produced in the supply chambers 25a and 26a is supplied to the dialyzer 2 via a dialysate supply path 27, and the used dialysate passing through an inside of the dialyzer 2 is recovered in the recovery chambers 25b and 26b via a dialysate recovery path 28.

The dialysate supply path 27 is branched and connected to the supply chambers 25a and 26a of the first and second dialysate chambers 25 and 26, and the dialysate recovery path 28 is also branched to be connected to the recovery chambers 25b and 26b.

Further, a clean water supply path 31 that supplies clean water to the supply chambers 25a and 26a of the first and second dialysate chambers 25 and 26, and a dialysate discharge path 32 for discharging used dialysate is connected to the recovery chambers 25b and 26b.

A liquid supply port 31A is an upstream side end portion of the clean water supply path 31 and is connected to water supplying means (not illustrated) that supplies clean water, and a downstream portion of the clean water supply path 31 is branched in two directions to be respectively connected to the supply chambers 25a and 26a of the first and second dialysate chambers 25 and 26, and these branches are respectively provided with liquid supply valves V1 and V2 opened and closed by control of the control means.

In the clean water supply path 31, a liquid feed pump 33 that feeds the clean water is provided, and a stock solution A supply path 34 that supplies the stock solution A that is a stock solution of dialysate, and a first stock solution B supply path 35 that supplies the stock solution B that is a stock solution of the dialysate are connected between the liquid feed pump 33 and the branch portion of the aforementioned clean water supply path 31.

An on-off valve V103 is provided in a position at a downstream side close to the liquid supply port 31A in the clean water supply path 31, and the on-off valve V103 has an operation controlled by the control means. When the liquid feed pump 33 is operated, the on-off valve V103 is also opened by the control means, and thereby, clean water can be fed to the supply chambers 25a and 26a of the first and second dialysate chambers 25 and 26 via the clean water supply path 31 from the liquid supply port 31A.

A stock solution A container 36 and a stock solution B container 37 are respectively connected to upstream portions of the stock solution A supply path 34 and the first stock solution B supply path 35, and the stock solution A and the stock solution B are respectively fed to the dialysate producing means 21 by a stock solution A pump 38 provided in the stock solution A supply path 34 and a stock solution B pump 39 provided in the first stock solution B supply path 35.

Further, instead of supplying the stock solution B from the stock solution B container 37, powder in a powder container 42 is dissolved in clean water by stock solution B producing means 41, and this can be supplied to the dialysate producing means 21 as the stock solution B.

The stock solution B producing means 41 includes the powder container 42 housing powder B to be the stock solution B, a branch path 43 that is branched from the clean water supply path 31 to supply clean water to the powder container 42, and a second stock solution B supply path 44 that supplies the stock solution B dissolved in the powder container 42 to the dialysate producing means 21.

One end of the branch path 43 is connected to the clean water supply path 31 between a downstream side of the liquid feed pump 33 and an upstream side of the stock solution A supply path 34 and the first stock solution B supply path 35, and the other end of the branch path 43 is caused to communicate with an upper space in the powder container 42.

Further, one end of the second stock solution B supply path 44 is caused to communicate with a lower space in the powder container 42, while the other end is connected to the first stock solution B supply path 35 at an upstream side from the stock solution B pump 39, on-off valves 45 and 46 for causing either one of the paths 35 and 44 to communicate with the stock solution B pump 39 are provided in the respective first stock solution B supply path 35 and the second stock solution B supply path 44.

Figure 2:
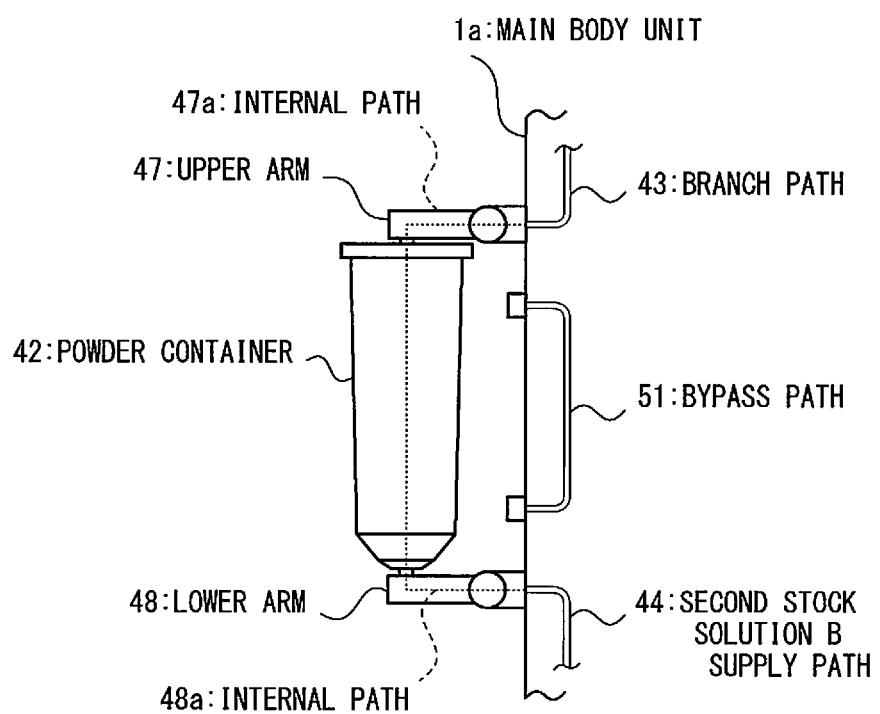
FIG. 2 is a view illustrating a state in which a powder container 42 is detachably attached between arms 47 and 48 in FIG. 1.

As illustrated in FIG. 2, the powder container 42 is attachably and detachably held at an outside of the main body unit 1a of the dialysis device 1. That is, an upper arm 47 and a lower arm 48 are provided in upper and lower positions outside the main body unit 1a, and the upper arm 47 is swingable between a holding position (FIG. 2) to be in a horizontal direction and a folded position (FIG. 1) to be vertically downward.

Further, the lower arm 48 is swingable between a holding position (FIG. 2) to be in the horizontal direction and a folded position (FIG. 1) to be vertically upward.

In a state where both the arms 47 and 48 are located in the holding positions in the horizontal direction, the powder container 42 can be held vertically between tip end portions of both the arms (state in FIG. 2).

In this state, the branch path 43 provided in the main body unit 1a communicates with an internal space of the powder container 42 from an upper portion thereof via an internal path 47a provided in the upper arm 47, and the second stock solution B supply path 44 communicates with the internal space of the powder container 42 from a lower portion thereof via an internal path 48a provided in the lower arm 48.

Thereby, clean water from the branch path 43 is supplied into the powder container 42 via the internal path 47a of the upper arm 47, and the stock solution B produced by being dissolved in the powder container 42 can be supplied to the second stock solution B supply path 44 via the internal path 48a in the lower arm 48.

Further, as illustrated in FIG. 3, on-off valves 49 and 50 are respectively provided in the branch path 43 at an upstream side of the powder container 42 and the second stock solution B supply path 44 at a downstream side, and the powder container 42 can be detached from the upper arm 47 and the lower arm 48 in a state where both the on-off valves 49 and 50 are closed.

In a state where the powder container 42 is detached from both the arms 47 and 48, and both the arms 47 and 48 are in a folded state as illustrated in FIG. 1, the internal path 47a in the upper arm 47 communicates with an upper end portion of a bypass path 51 provided inside the main body unit 1a, and the internal path 48a in the lower arm 48 communicates with a lower end portion of the bypass path 51.

Thereby, clean water and a cleaning solution from the branch path 43 can be caused to flow in the second stock solution B supply path 44 via the internal path 47a in the upper arm 47, the bypass path 51 and the internal path 48a in the lower arm 48.

Next, in the dialysate supply path 27, an upstream portion thereof is branched in two directions to be respectively connected to the supply chambers 25a and 26a of the first and second dialysate chambers 25 and 26, and supply valves V3 and V4 that are opened and closed by control of the control means are respectively provided in the branched portions. A coupler 27A attachable to and detachable from the dialyzer 2 is coupled to a downstream side end portion of the dialysate supply path 27, and the coupler 27A is connected to the dialyzer 2 at a time of dialytic treatment.

Further, in the dialysate supply path 27, a dialysate filter F1 that removes harmful components in the dialysate, and an on-off valve V5 that is opened and closed by control of the control means are provided in order from the branch point. To a primary side of the dialysate filter F1, a bypass path 55 that causes the dialysate supply path 27 and the dialysate recovery path 28 to communicate with each other is connected, and in the bypass path 55, an on-off valve V6 that is opened and closed by control of the control means is provided.

By opening the on-off valve V6, the dialysate in the dialysate supply path 27 can be fed to the dialysate recovery path 28 via the bypass path 55 without causing the dialysate to pass through the dialyzer 2.

In the dialysate recovery path 28, a downstream portion thereof is branched in two directions to be respectively connected to the recovery chambers 25b and 26b of the first and second dialysate chambers 25 and 26, and in the branched portions, recovery valves V10 and V11 that are opened and closed by control of the control means are respectively provided. Further, a coupler 28A is coupled to an upstream side end portion of the dialysate recovery path 28, and the coupler 28A can be connected to the dialyzer 2 attachably and detachably.

Further, the coupler 28A of the dialysate recovery path 28 and the coupler 27A of the dialysate supply path 27 are both detached from the dialyzer 2, and thereafter both the couplers 27A and 28A are connected to each other, whereby the dialysate supply path 27 and the dialysate recovery path 28 can be caused to communicate with each other (state shown by the broken line in FIG. 3).

Further, in the dialysate recovery path 28, a pressure sensor 56 that measures pressure in the dialysate circuit 4 and a dialysate pump 57 that feeds the dialysate are provided in order from a side of the dialyzer 2.

In the dialysate discharge path 32, an upstream portion thereof is branched in two directions to be respectively connected to the recovery chambers 25b and 26b of the first and second dialysate chambers 25 and 26, and liquid discharge valves V12 and V13 that are opened and closed by control of the control means are respectively provided in the branched portions. A liquid discharge port 32A that is a downstream end of the dialysate discharge path 32 is connected to a liquid discharge pipe (not illustrated) installed in a medical institution. Further, in a position at an upstream side close to the liquid discharge port 32A in the dialysate discharge path 32, an on-off valve V104 that is opened and closed by the control means is disposed.

A water removal path 58 is connected between the dialysate recovery path 28 and the dialysate discharge path 32 at the upstream side from the on-off valve V104, and an upstream portion thereof is connected between a dialysate pump 57 in the dialysate recovery path 28 and the branch point, and a downstream portion is connected to a downstream side of the branch point in the dialysate discharge path 32. In the water removal path 58, a water removal pump 59 is provided.

The above configuration is a conventionally known configuration, and when hemodialysis is carried out by using the powder container 42, a process as follows is performed.

First, the on-off valve V103 and the on-off valve V104 are opened by the control means, and both the couplers 27A and 28A of the dialysate circuit 4 are connected to the dialyzer 2 in advance. Further, the on-off valve 45 is closed while the on-off valve 46 is opened, use of the powder container 42 is selected, instead of the stock solution B container 37, and the on-off valves 49 and 50 are opened to bring about a state capable of supplying clean water into the powder container 42.

In this state, the control means opens the liquid supply valve V1 and the liquid discharge valve V12, and closes the supply valve V3 and the recovery valve V10. Further, the control means operates the liquid feed pump 33, the stock solution A pump 38 and the stock solution B pump 39 at a predetermined timing.

When the liquid feed pump 33 is actuated, a part of clean water is supplied into the powder container 42 via the branch path 43, and thereby the stock solution B is produced in the powder container 42. Further, since the liquid supply valve V1 and the liquid discharge valve V12 are opened in the first dialysate chamber 25, the stock solution A in the stock solution A container 36 and the stock solution B in the powder container 42 are supplied to the supply chamber 25a due to actuation of the stock solution A pump 38 and stock solution B pump 39, and clean water is supplied from the liquid feed pump 33.

Thereby, the stock solution A, the stock solution B and clean water are mixed in the supply chamber 25*a* configuring the dialysate producing means 21 and fresh dialysate is produced, whereas in the recovery chamber 25*b*, the diaphragm is pressed and the used dialysate previously charged is discharged to an outside via the dialysate discharge path 32 and the liquid discharge port 32A thereof.

On the other hand, in the second dialysate chamber 26, the control means opens the supply valve V4 and the recovery valve V11, and closes the liquid supply valve V2 and the liquid discharge valve V13. Then, the used dialysate which is fed by the dialysate pump 57 flows into the recovery chamber 26*b*, and a produced fresh dialysate is supplied to the dialyzer 2 from the supply chamber 26*a*.

Thereafter, the control means alternately opens and closes the liquid supply valves V1 and V2, the supply valves V3 and V4, the recovery valves V10 and V11, and the liquid discharge valves V12 and V13, whereby the fresh dialysate produced alternately in the first dialysate chamber 25 and the second dialysate chamber 26 is supplied to the dialyzer 2 via the dialysate supply path 27, and the used dialysate passing through the dialyzer 2 is alternately recovered by the first dialysate chamber 25 and the second dialysate chamber 26 and is discharged to the outside of the dialysate circuit 4 via the liquid discharge port 32A of the dialysate discharge path 32.

By operating the water removal pump 59 while feeding the dialysate continuously to the dialyzer 2 in this way, water removal can be performed.

When the powder container 42 is directly detached from both the arms 47 and 48 after the aforementioned hemodialysis operation is finished, the stock solution B remaining in the powder container 42 leaks to the outside.

Further, when cleaning of the dialysate circuit 4 is performed before the hemodialysis operation, cleaning is performed in a state where both the arms 47 and 48 are folded, and the internal path 47*a* of the upper arm 47 and the internal path 48*a* of the lower arm 48 are caused to communicate with each other via the bypass path 51, and when both the arms 47 and 48 are separated from the bypass path 51 and the powder container 42 is attached thereafter, clean water and a cleaning solution in the bypass path 51 leaks to the outside.

The present invention can prevent occurrence of the aforementioned situation by draining a residual liquid remaining in the powder container 42 and the bypass path 51.

That is, in order to drain the residual liquid remaining in the powder container 42 and the bypass path 51, a first liquid draining path 71 that causes the second stock solution B supply path 44 and the clean water supply path 31 to communicate with each other is provided, and a second liquid draining path 72 that connects the clean water supply path 31 and the dialysate discharge path 32 is provided.

One end of the first liquid draining path 71 is connected to the second stock solution B supply path 44 between the on-off valve 46 and the on-off valve 50 provided in the second stock solution B supply path 44, and the other end of the first liquid draining path 71 is connected to the clean water supply path 31 at an upstream side of the liquid feed pump 33 provided in the clean water supply path 31. An on-off valve 73 is provided in the first liquid draining path 71.

On the other hand, one end of the second liquid draining path 72 is connected to the clean water supply path 31 at a downstream side of the liquid feed pump 33, and the other end of the second liquid draining path 72 is connected to the dialysate discharge path 32 at a downstream side of the on-off valve V104 provided in the dialysate discharge path 32. An on-off valve 74 is provided in the second liquid draining path 72.

Further, at an upstream side of the powder container 42, an opening path 77 that opens the closed dialysate circuit 4 to the atmosphere is provided. One end of the opening path 77 is connected to the branch path 43 at a downstream side of the on-off valve 49 provided in the branch path 43, and the other end is open to the atmosphere. In the opening path 77, from the one end to the other end, an on-off valve 78 that is opened and closed by control of the control means, a check valve 79 that inhibits an outflow of the liquid and an air filter 80 that cleans the air that flows in are provided.

When the on-off valve 78 is opened by the control means, air is capable of flowing in the branch path 43 configuring the closed circuit via the opening path 77, and at this time, the atmosphere flowing into the branch path 43 is cleaned by the air filter 80, whereas the check valve 79 inhibits an outflow of the liquid.

Further, in the present embodiment, in order to detect that liquid draining in the powder container 42 and the bypass path 51 is finished, the pressure sensor 56 provided in the dialysate recovery path 28 can be used. For this purpose, one end of a pressure detection path 83 is connected between the pressure sensor 56 and the dialysate pump 57 provided in the dialysate recovery path 28, and the other end of the pressure detection path 83 is connected between the first liquid draining path 71 and the on-off valve V103, at an upstream side of the liquid feed pump 33 provided in the clean water supply path 31. An on-off valve 84 is provided in the pressure detection path 83.

Thereby, while the liquid feed pump 33 feeds the liquid (while performing liquid draining), the pressure of the pressure sensor 56 becomes a low pressure as compared with the pressure in a state before the liquid draining is started, but when liquid draining is finished and the liquid feed pump 33 involves air, the pressure of the pressure sensor 56 rises from the state in which the pressure of the pressure sensor 56 becomes the low pressure, so that the control means can thereby detect that the liquid draining is finished.

In the above configuration, when the powder container 42 is detached after the end of the dialytic treatment by the dialysis device 1, the control means opens the on-off valve 50 of the second stock solution B supply path 44, the on-off valve 73 of the first liquid draining path 71, and the on-off valve 74 of the second liquid draining path 72, and opens on-off valve 78 of the opening path 77 and the on-off valve 84 of the pressure detection path 83. The other valves are all closed.

When the liquid feed pump 33 is actuated in this state, the stock solution B in the powder container 42 is discharged to the outside via the second stock solution B supply path 44, the first liquid draining path 71, the clean water supply path 31, the liquid feed pump 33, the second liquid draining path 7 and the dialysate discharge path 32, and at the same time as this, air flows into the powder container 42 via the opening path 77.

Further, when liquid draining is started by actuation of the liquid feed pump 33, a liquid pressure in the pressure detection path 83 and the dialysate recovery path 28 becomes a low pressure as compared with the pressure in the state before the liquid draining is started as described above, with liquid discharge in the clean water supply path 31, and the low pressure is detected by the pressure sensor 56.

When liquid draining in the powder container 42 advances, and air reaches the liquid feed pump 33 via the second stock solution B supply path 44, the first liquid draining path 71 and the clean water supply path 31, liquid feeding by the liquid feed pump 33 cannot be performed. Thereby, the liquid pressure in the pressure detection path 83 and the dialysate recovery path 28 rises from the aforementioned low pressure state.

The control means stores the pressure in the low-pressure state after a lapse of a required time by measuring the pressure by the pressure sensor 56 after actuation of the liquid feed pump 33, and when air reaches the liquid feed pump 33 and the pressure rises, the control means determines that liquid draining in the powder container 42 is finished, and stops the liquid feed pump 33. At the same time as this, the control means displays on the operation panel 1b that liquid draining in the powder container 42 is finished.

In this state, liquid leakage does not occur from the inside of the powder container 42 even when the powder container 42 is detached from the upper and lower arms 47 and 48. The aforementioned explanation similarly applies to the case of liquid draining from the bypass path 51.

At the time of liquid draining in either case, the liquid feed pump 33 having a large liquid feed amount is used, so that the liquid draining operation can be finished quickly.

Note that in the above described embodiment, the stock solution B container 37 is provided, but the stock solution B container 37 and the first stock solution B supply path 35 may be omitted.

Further, in the above described embodiment, the pressure sensor 56 provided in the dialysate recovery path 28 is used to detect that liquid draining in the powder container 42 and the bypass path 51 is finished, but it may be determined that the liquid draining is finished after a lapse of a required time by using a timer.

The invention claimed is:

1. A dialysis device comprising:
   a main body unit;
   a dialyzer connected to the main body unit;
   a blood circuit having a first path connected to the dialyzer to supply blood thereto from a patient and a second path connected to the dialyzer to return blood to the patient from the dialyzer;
   an operation panel having a display screen and at least one of buttons, icons and/or messages for operation of the dialysis device;
   a dialysate circuit provided inside the main body unit, the dialysate circuit comprising:
   a clean water supply path connected to a clean water supply;
   a liquid feed pump provided in the clean water supply path;
   a powder container containing dialysate producing powder therein;
   a stock solution supply path connected to the powder container;
   a branch path connected to the clean water supply path and the stock solution supply path, the powder container being attachably and detachably connected to the branch path, the dialysate producing powder in the powder container being dissolved by clean water supplied to the powder container from the branch path to produce a stock solution of dialysate;
   a dialysate supply path connected to the stock solution supply path and to the dialyzer, the dialysate supply path supplying the stock solution of dialysate from the stock solution supply path mixed with clean water from the liquid feed pump to the dialyzer, the stock solution of dialysate mixed with the clean water comprising dialysate;
   a dialysate discharge path connected to the dialyzer for discharging used dialysate therefrom;
   a first liquid draining path connecting the clean water supply path at an upstream side of the liquid feed pump to the stock solution supply path;
   a second liquid draining path connecting the clean water supply path at a downstream side of the liquid feed pump to the dialysate discharge path;
   an opening path connected to the branch path and configured to open the dialysate circuit to the atmosphere through the branch path; and
   a valve provided in the opening path, the valve having an open position in which the branch path is in communication with the atmosphere and a closed position in which the branch path is not in communication with the atmosphere, and the valve in the open position permits draining of a liquid in the powder container via the first liquid draining path, the second liquid draining path and the dialysate discharge path when the liquid feed pump is operated to prevent leakage of liquid in the powder container when the powder container is detached from the branch path and the stock solution supply path.

2. The dialysis device according to claim 1, wherein the dialysate circuit further comprises a dialysate chamber and a dialysate recovery path, the dialysate chamber having an interior divided into a supply chamber and a recovery chamber, the dialysate supply path supplying the dialysate to the dialyzer from the supply chamber of the dialysate chamber, used dialysate from the dialyzer is recovered into the recovery chamber of the dialysate chamber via the dialysate recovery path and the dialysate discharge path discharges used dialysate recovered in the recovery chamber to an outside.

3. The dialysis device according to claim 2, wherein the dialysate circuit further comprises a pressure sensor disposed in the dialysate recovery path, the pressure sensor being configured to detect pressure in the dialysate recovery path and to produce a detected pressure for stopping operation of the liquid feed pump, and a pressure detection path connecting the clean water supply path and the dialysate recovery path at an upstream side of a connection portion of the clean water supply path and the first liquid draining path.

4. The dialysis device according to claim 1, wherein the powder container interconnects the branch path and the stock solution supply path to one another, the dialysate circuit further comprising a bypass path connecting the stock solution supply path and the branch path to one another when the powder container is detached from the stock solution supply path and the branch path, the valve in the open position permitting draining of a liquid in the bypass path via the first liquid draining path and the second liquid draining path when the powder container is detached from the branch path and the stock solution supply path and when the liquid feed pump is operated.

5. The dialysis device according to claim 1, wherein the powder container interconnects the branch path and the stock solution supply path to one another, and the dialysate circuit further comprises:

a dialysate recovery path, a pressure sensor disposed in the dialysate recovery path, a pressure detection path connecting the clean water supply path and the dialysate recovery path at an upstream side of a connection between the clean water supply path and the first liquid draining path;

a dialysate producing arrangement including a dialysate chamber divided into a supply chamber and a recovery chamber, the dialysate supply path being configured to supply the dialysate to the dialyzer from the supply chamber, used dialysate from the dialyzer being recovered into the recovery chamber through the dialysate recovery path, and the dialysate discharge path is configured to discharge used dialysate recovered in the recovery chamber to the outside; and a stock solution producing arrangement including a bypass path, the powder container, the branch path and the stock solution supply path, the bypass path connecting the stock solution supply path and the branch path to one another when the powder container is detached from the stock solution supply path and the branch path, the stock solution producing arrangement supplying the stock solution of dialysate to the dialysate producing arrangement via the stock solution supply path.

* * * * *